(12) United States Patent
Hutchison

(10) Patent No.: US 9,254,079 B2
(45) Date of Patent: Feb. 9, 2016

(54) ILLUMINATION SOURCE AND METHOD FOR USE WITH IMAGING DEVICE

(71) Applicant: Topcon Medical Laser Systems, Inc., Santa Clara, CA (US)

(72) Inventor: Sheldon Hutchison, Sunnyvale, CA (US)

(73) Assignee: Topcon Medical Laser Systems, Inc., Santa Clara, CA (US)

( * ) Notice: Subject to any disclaimer, the term of this patent is extended or adjusted under 35 U.S.C. 154(b) by 157 days.

(21) Appl. No.: 14/153,818

(22) Filed: Jan. 13, 2014

(65) Prior Publication Data

US 2015/0196198 A1   Jul. 16, 2015

(51) Int. Cl.

| | |
|---|---|
| A61B 3/10 | (2006.01) |
| A61B 3/00 | (2006.01) |
| A61B 3/14 | (2006.01) |
| F21V 5/04 | (2006.01) |
| A61B 3/12 | (2006.01) |
| A61B 3/13 | (2006.01) |
| A61B 3/135 | (2006.01) |
| G02B 3/08 | (2006.01) |

(52) U.S. Cl.
CPC ............... *A61B 3/0008* (2013.01); *A61B 3/12* (2013.01); *A61B 3/13* (2013.01); *A61B 3/135* (2013.01); *A61B 3/14* (2013.01); *F21V 5/045* (2013.01); *G02B 3/08* (2013.01)

(58) Field of Classification Search
CPC ............ A61B 3/12; A61B 3/13; A61B 3/135; A61B 3/14
USPC .......................................... 351/214, 205, 221
See application file for complete search history.

(56) References Cited

U.S. PATENT DOCUMENTS

| 4,733,944 A | 3/1988 | Fahlen et al. |
| 5,523,809 A * | 6/1996 | Kohayakawa ................. 351/211 |

(Continued)

FOREIGN PATENT DOCUMENTS

| CN | 102901045 A | 1/2013 |
| EP | 1114608 A1 | 7/2001 |
| EP | 1875857 A1 | 1/2008 |

OTHER PUBLICATIONS

International Search Report and Written Opinion mailed on Apr. 2, 2015, in connection with International Patent Application No. PCT/US15/10009, 11 pgs.

Sramek et al., "Enhanced Safety of Retinal Photocoagulation by Spatial or Temporal Modulation of Laser Power," no publication date, 1 pg.

(Continued)

*Primary Examiner* — Hung Dang
(74) *Attorney, Agent, or Firm* — Chiesa Shahinian & Giantomasi PC

(57) ABSTRACT

A system includes a first element configured to receive a plurality of color components that are spatially separated, wherein each of the plurality of color components comprises light of a respective wavelength, and to focus the plurality of spatially separated color components onto a first surface of a second element. The system also includes a second element having a first surface and a second surface, wherein the second element is configured to receive the plurality of color components via the first surface, to transmit to the second surface uniform light comprising the plurality of color components in a blended state, and to emit the uniform light via the second surface. The system also includes a slit lamp configured to receive the uniform light.

20 Claims, 8 Drawing Sheets

(56) References Cited

U.S. PATENT DOCUMENTS

| | | |
|---|---|---|
| 7,599,591 B2 | 10/2009 | Andersen et al. |
| 2006/0100677 A1 | 5/2006 | Blumenkranz et al. |
| 2007/0129775 A1 | 6/2007 | Mordaunt et al. |
| 2010/0168724 A1 | 7/2010 | Sramek et al. |
| 2010/0214535 A1 | 8/2010 | Wada et al. |

OTHER PUBLICATIONS

Sramek et al., "Improving the Therapeutic Window of Retinal Photocoagulation by Spatial and Temporal Modulation of the Laser Beam," Journal of Biomedical Optics, vol. 16, No. 2, Feb. 2011, pp. 028004-1-028004-12.

* cited by examiner

ILLUMINATION SOURCE AND METHOD FOR USE WITH IMAGING DEVICE

TECHNICAL FIELD

This specification relates generally to ophthalmic imaging systems and methods for use in diagnosing and treating conditions of the eye, and more particularly to imaging systems and methods for use with slit lamps, surgical microscopes, direct ophthalmoscopes or indirect ophthalmoscopes.

BACKGROUND

The slit lamp is an instrument consisting of a high-intensity light source that can be focused to shine a beam of light into a patient's eye. The slit lamp allows a practitioner to obtain an image of selected structures in the patient's eye, thereby facilitating an examination and diagnosis of medical conditions. Slit lamp-mounted laser delivery devices are also commonly used for laser light treatments, including, for example, photocoagulative treatment for conditions such as age-related macular degeneration.

SUMMARY

In accordance with an embodiment, a system includes a first element that receives a plurality of spatially separated color components, wherein each of the plurality of color components comprises light of a respective wavelength, and focuses the plurality of spatially separated color components onto a first surface of a second element. The system also includes a second element having a first surface and a second surface, which receives the plurality of color components via the first surface, transmits to the second surface uniform light comprising the plurality of color components in a blended state, and emits the uniform light via the second surface.

In one embodiment, the system also includes a multiple-color light source that generates a plurality of spatially separated color components. The multiple-color light source may further include a plurality of light sources, each of which generates a color component associated with a respective wavelength, and a controller to control an intensity of the color component generated by one or more of the light sources. The plurality of light sources may include a plurality of LED light sources.

In another embodiment, the plurality of light sources include a first light source that generates a first color component associated with a red wavelength, a second light source that generates a second color component associated with a green wavelength, a third light source that generates a third color component associated with a blue wavelength, and a fourth light source that generates a fourth color component associated with an amber wavelength.

In one embodiment, the imaging system is a slit lamp. The second surface of the second element may provide a reference plane for an optical element of an imaging system. The optical element may be a lens or a mirror, for example.

In another embodiment, the first element has a central point and a plurality of facets arranged concentrically around the central point. Each facet has a respective height, and the heights of the facets varies based on a distance from the central point. In one embodiment, at least one facet has an inner side that is vertical and a second side that has a sloping configuration.

In accordance with another embodiment, a method is provided. A plurality of spatially separated color components are received by a first element. The plurality of spatially separated color components are focused, by the first element, onto a first surface of a second element. The plurality of color components are blended, by the second element, to generate uniform light comprising the plurality of spatially separated color components in a blended state. The uniform light is emitted, by the second element, via a second surface of the second element, wherein the second surface provides a reference plane for an optical element of an imaging system.

In one embodiment, a plurality of spatially separated color components are generated by a multiple color light source. An input is received, and an intensity of one of the first, second, and third color components is varied based on the input. The imaging system may be a slit lamp, for example.

In accordance with another embodiment, a system includes a light source configured to generate a plurality of spatially separated color components, and a first element comprising a transmissive material and a plurality of facets, the first element being configured to refract the plurality of spatially separated color components onto a surface of a second element. The system also includes a second element comprising a transmissive material, the second element being configured to blend the plurality of color components to produce uniform light, and to provide the uniform light to a slit lamp. The system also includes a slit lamp. The light source is further configured to receive an input indicating a change in an intensity of a selected one of the plurality of spatially separated color components, and to modify the intensity of the selected one of the plurality of spatially separated color components, based on the input. In one embodiment, the light source is a multiple color light source comprising a plurality of LED light sources.

In one embodiment, the first element comprises a focusing homogenizer and the second element comprises a focusing filament.

These and other advantages of the present disclosure will be apparent to those of ordinary skill in the art by reference to the following Detailed Description and the accompanying drawings.

DETAILED DESCRIPTION

Figure 1:
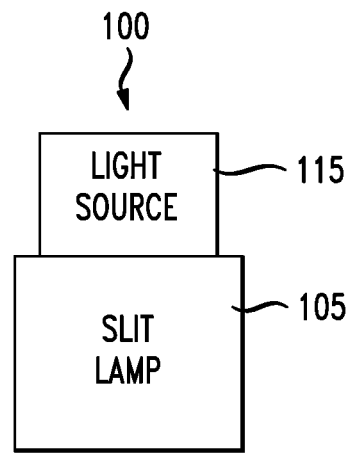
FIG. 1 shows an exemplary imaging system.

FIG. 1 shows an exemplary imaging system 100. Imaging system 100 comprises a light source 115 and a slit lamp 105. Light source 115 generates light for use in slit lamp 105. Light source 115 may also provide a reference plane for one or more optical elements of an optical system within slit lamp 105. For example, light source 115 may provide a reference plane for a lens or mirror within slit lamp 105.

Slit lamp 105 may be any type of commonly used slit lamp. For example, slit lamp 105 may be a SL-D7 slit lamp manufactured by Topcon Corporation, located in Tokyo, Japan. Alternatively, other slit lamps may be used, such as a Topcon SL-D3 slit lamp, a Topcon SL-D4 slit lamp, a Topcon OMS-710 surgical microscope, a Topcon Laser Indirect Ophthalmoscope, etc. Use of slit lamps is known.

Many current slit-lamp-based delivery systems use a light source, such as a halogen light source, that produces and channels white light to the slit lamp via one or more optical fibers.

The use of white light does not permit a practitioner to control with precision the color of the light that enters the slit lamp, and therefore limits the range of observations that can be made by the practitioner. For example, it is sometimes advantageous to observe certain structures of the eye, and/or certain medical conditions, using selected colors of light. Existing delivery systems use one or more color filters to control the color of light delivered to the eye, in order to facilitate the observation of certain aspects of the eye that may be difficult to visualize under white light. For example, filters may be used to produce red, blue, or green light, to remove infrared light, etc. Even with the use of filters, the practitioner is limited by the filters currently available and therefore may not be able to achieve a desired level of precision in the selection of the color of light used.

Use of an imaging system that allows a practitioner to control the color(s) that enter the slit lamp, and the patient's eye, with greater ease and precision would be advantageous as it would facilitate improved observation and diagnosis.

In accordance with an embodiment, an improved slit lamp-based imaging system comprises a slit lamp and a multiple color light source that generates multiple components of light. The multiple color light source may be controlled to determine the colors of light that enter the slit lamp and the patient's eye. In addition, the imaging system includes a focusing element that focuses and blends the various components of light and emits uniform light for use by the slit lamp.

Figure 2:
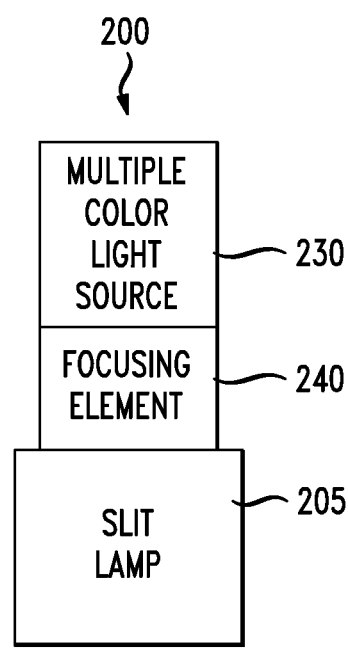
FIG. 2 shows a slit lamp-based imaging system in accordance with an embodiment.

FIG. 2 shows a slit lamp-based imaging system 200 in accordance with an embodiment. Imaging system 200 comprises a slit lamp 205, a multiple color light source 230, and a focusing element 240.

Slit lamp 205 may be any type of slit lamp. For example, slit lamp 205 may be a SL-D7 slit lamp manufactured by Topcon Corporation, located in Tokyo, Japan. Alternatively, other slit lamps may be used, such as a Topcon SL-D3 slit lamp, a Topcon SL-D4 slit lamp, a Topcon OMS-710 surgical microscope, a Topcon Laser Indirect Ophthalmoscope, etc. Other types of slit lamps, or other delivery devices or systems, may be used.

Multiple color light source 230 comprises a plurality of light sources, each producing a color component associated with a respective range of colors or wavelengths (e.g., red, green, blue, amber, etc.). The color components generated by multiple color light source 230 are spatially separated. For example, in one embodiment, multiple color light source 230 comprises a red light source, a green light source, and a blue light source that are separated from one another by a distance of 0.1 millimeters. Accordingly, multiple color light source 230 generates three separate beams of red, green, and blue light that are separated from one another by 0.1 millimeters when they are emitted. In other embodiments, multiple color light source 230 may also comprise a light source that produces a component of non-visible radiation, such as infrared or ultraviolet radiation.

Focusing element 240 receives and focuses the various components of light produced by multiple color light source 230, and blends the color components to produce light in which the various color components are in a blended state (not spatially separated). Focusing element 240 emits uniform light comprising the blended color components. Focusing element 240 also provides a reference plane for one or more optical elements of slit lamp 220, such as a lens or mirror. The optical element(s) of slit lamp 220 may therefore utilize the reference plane as a point source.

Multiple Color Light Source

Multiple color light source 230 may have any number of light sources which produce respective color components that are spatially separated. In an embodiment shown in FIG. 3A, a multiple color light source 230-A is an RGB light-emitting diode (LED) light source. Accordingly, multiple color light source 230-A comprises a red LED light source 322 that generates light in a range of wavelengths associated with the color red, a green LED light source 324 that generates light in a range of wavelengths associated with the color green, and a blue LED light source 326 that generates light in a range of wavelengths associated with the color blue. The ranges of wavelengths produced by each light source may vary.

Multiple color light source 230-A also comprises a controller 380-A and an interface 381-A. Controller 380-A controls red LED light source 322, green LED light source 324, and blue LED light source 326. Interface 381-A receives input from a practitioner. For example, interface 381-A may include one or more buttons, dials, switches, or digital controls (e.g., indicators on a touch-screen) that enable a practitioner to control the intensity of each light source 322, 324, 326. For example, controller 380-A may turn on, or turn off, or vary the intensity of, light sources 322, 324, 326 in response to input from a practitioner. Accordingly, a practitioner may select a desired combination of red, green, and blue wavelengths by controlling the intensity of light sources 322, 324, 326.

Figure 3A:
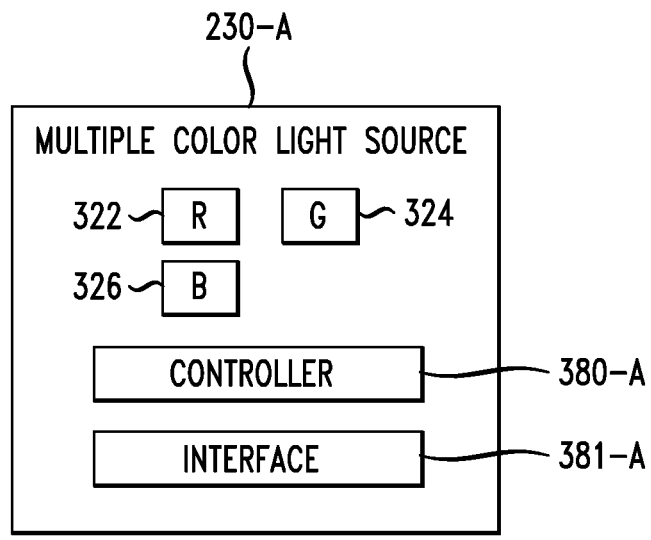
FIG. 3A shows a three-color light source in accordance with an embodiment.
Figure 3B:
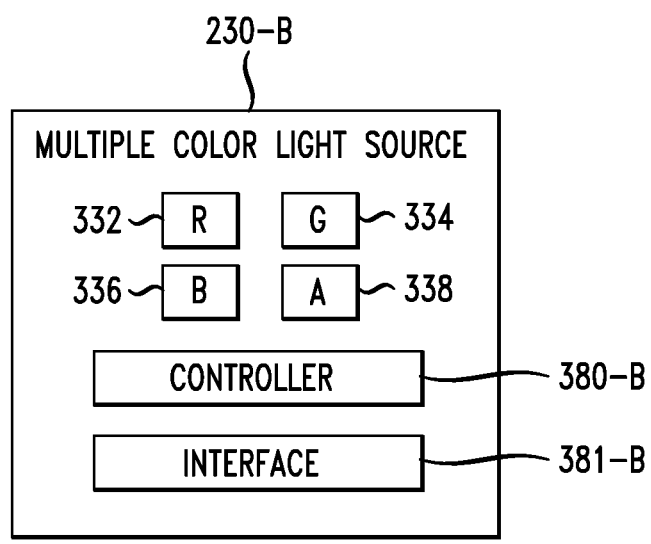
FIG. 3B shows a four-color light source in accordance with an embodiment.

In another embodiment shown in FIG. 3B, a multiple color light source 230-B is an RGBA light-emitting diode (LED) light source. Accordingly, multiple color light source 230-B comprises a red LED light source 332, a green LED light source 334, a blue LED light source 336, and an amber LED light source 338.

In one embodiment, red LED light source 332 generates light in a range of wavelengths associated with the color red, green LED light source 334 generates light in a range of wavelengths associated with the color green, blue LED light source 336 generates light in a range of wavelengths associated with the color blue, and amber LED light source 338 generates light in a range of wavelengths associated with the color amber.

Multiple color light source 230-B also comprises a controller 380-B and an interface 381-B. Controller 380-B controls red LED light source 332, green LED light source 334, blue LED light source 336, and amber LED light source 338. Interface 381-B receives input from a practitioner. For example, interface 381-B may include one or more buttons, dials, switches, or digital controls (e.g., indicators on a touchscreen) that enable a practitioner to control the intensity of each light source 332, 334, 336, 338. For example, controller 380-B may turn on, or turn off, or vary the intensity of, light sources 332, 334, 336, 338 in response to input from a practitioner. Accordingly, a practitioner may select a desired combination of red, green, blue, and amber wavelengths by controlling the intensity of light sources 332, 334, 336, 338.

While in the embodiments of FIGS. 3A and 3B, multiple color light sources 230-A and 230-B include, respectively, three and four LED light sources, in other embodiments, multiple color light source 230 may comprise fewer than three, or more than four, LED light sources, of any color combination.

For convenience, certain functions, features, and advantages of multiple color light source 230 are described below with reference to multiple color light source 230-B of FIG. 3B; however, the discussion below is equally applicable to multiple color light source 230-A and to other embodiments.

Referring to FIG. 3B, each color source of multiple color light source 230-B may be individually controlled in order to select a desired color for the light that enters a patient's eye. For example, a practitioner may modulate red LED light source 332 to increase or decrease the red component in the light that enters the patient's eye.

A multiple color light source such as that shown in FIG. 3B may advantageously provide finer control over the wavelengths entering the patient's eye than is possible using existing systems. For example, controlling the colors/wavelengths of light used in a slit lamp system may advantageously facilitate high-contrast visualization of the retina. Controlling the colors/wavelengths of light used in a slit lamp system may also advantageously facilitate visualization of drug interaction (where a drug enters the retina). Such a multiple color light source may also be less costly and more convenient than existing systems as it eliminates the need to utilize filters and adjustment mechanisms.

Because the color components emitted by multiple color light source 230-B are in a spatially separated state, it is desirable to blend the different color components produced by the various light sources and produce uniform light that can be used by slit lamp 220. Referring again to the embodiment of FIG. 2, the multiple spatially separated color components produced by multiple color light source 230 are received by focusing element 240. Focusing element 240 blends the spatially separated color components to produce uniform light. Focusing element 240 also directs the uniform light toward slit lamp 205, providing a reference plane for the optical system of slit lamp 205. As used herein, a reference plane is defined as a plane in space, the light from which an optical component such as a lens or mirror is configured to bring into focus at a focal plane. A reference plane is sometimes referred to as an object plane.

For example, referring to FIG. 3B, red light produced by red LED light source 332, green light produced by green LED light source 334, blue light produced by blue LED light source 336, and amber light produced by amber LED light source 338 may be received by focusing element 240 and blended by focusing element 240 to generate uniform light. Focusing element 240 emits the uniform light toward slit lamp 205.

Focusing Element

Figure 4:
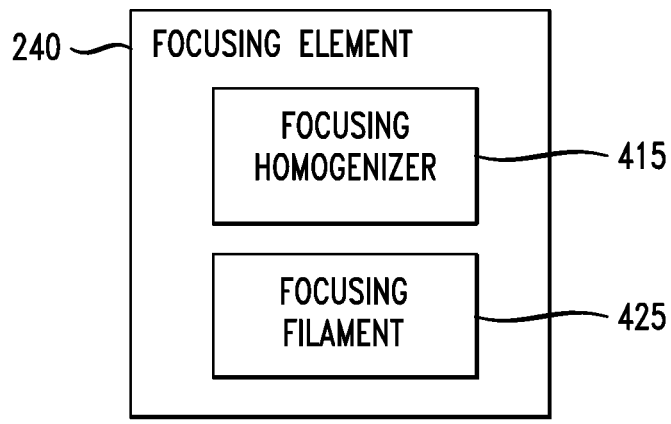
FIG. 4 shows components of a focusing element in accordance with an embodiment.

FIG. 4 shows components of focusing element 240 in accordance with an embodiment. Focusing element 240 comprises a focusing homogenizer 415 and a focusing filament 425.

Figure 5:
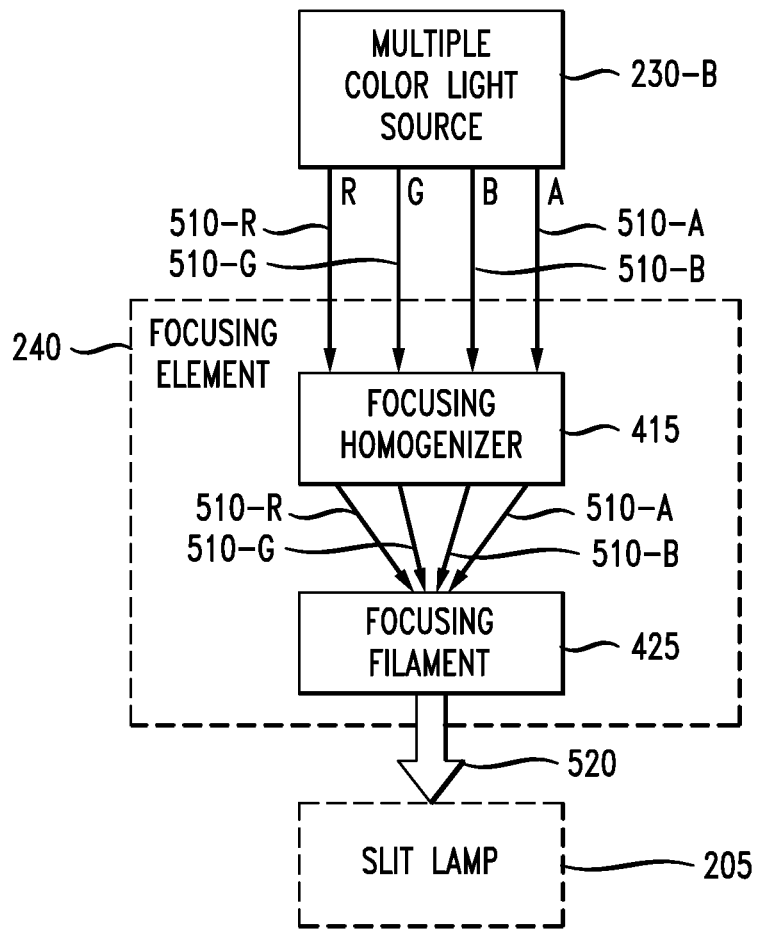
FIG. 5 is a schematic illustration of the functions performed by a multiple color light source, a focusing homogenizer, and a focusing filament in accordance with an embodiment.

FIG. 5 is a schematic illustration of the functions performed by multiple color light source 230-B, focusing homogenizer 415, and focusing filament 425 in accordance with an embodiment. FIG. 5 is illustrative only and is not to be construed as limiting with respect to the configuration or function of the components shown.

Multiple color light source 230-B generates a red color component 510-R, a green color component 510-G, a blue color component 510-B, and an amber color component 510-A. These color components may be emitted as separate beams of light, for example. These color components are transmitted, through the air, for example, and received by focusing homogenizer 415. Focusing homogenizer 415 receives color components 510 in a first, spatially separated state. Focusing homogenizer 415 focuses the color components onto a first surface of focusing filament 425. In one embodiment, focusing homogenizer 415 focuses the color components in such a manner that the color components overlap in a selected region of the first surface of focusing filament 425. Focusing filament 425 blends color components 510-R, 510-G, 510-B, and 510-A to produce uniform light (in which the color components are in a second, blended state). Focusing filament 425 emits the uniform light via a second surface as uniform light 520, toward slit lamp 205. As a result, the second surface of focusing filament 425 may function as a reference plane for one or more elements of the optical system of slit lamp 205. For example, slit lamp 205 may comprise one or more lenses; a surface of focusing filament 425 may provide a reference plane for a lens disposed in slit lamp 205.

The structures of focusing homogenizer 415 and focusing filament 425 are described in more detail below.

Focusing Homogenizer

Figure 6A:
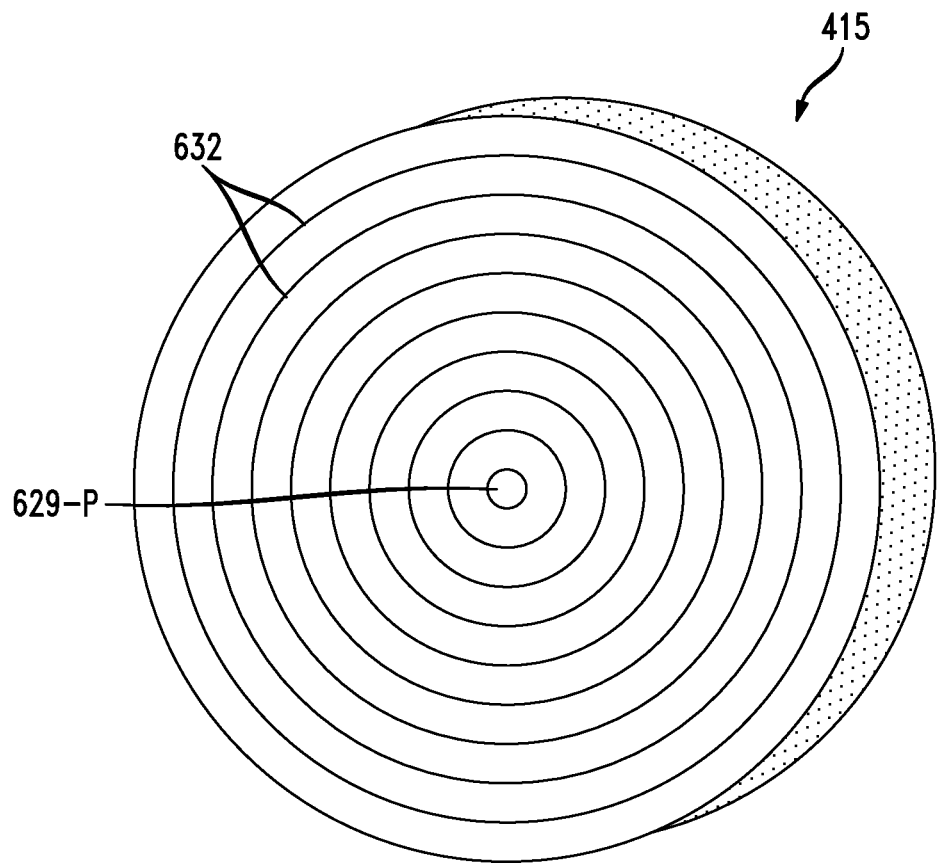
FIG. 6A shows a focusing homogenizer in accordance with an embodiment.

FIG. 6A shows focusing homogenizer 415 in accordance with an embodiment. Focusing homogenizer 415 comprises a circular lens comprising a clear material. For example, focusing homogenizer 415 may comprise glass, plastic, etc. In one embodiment, focusing homogenizer 415 comprises a transparent thermoplastic such as poly(methyl methacrylate) (PMMA). In other embodiments, focusing homogenizer 415 may comprise other types of material. In other embodiments, focusing homogenizer 415 may have a different shape.

Focusing homogenizer 415 comprises a series of facets 632 similar to those of a Fresnel lens. Fresnel lenses are known. In the embodiment of FIG. 6A, facets 632 are arranged concentrically around a central point 629-P associated with a central axis of focusing homogenizer 415. In other embodiments, facets 632 may be arranged differently. Similar to the operation of a Fresnel lens, facets 632 refract incoming light and focus the light at a defined focal point or focal plane. In particular, facets 632 correct for the spatial separation between the color components produced by multiple color light source 230 and cause the various color components to overlap at the defined focal point or focal plane.

Focusing homogenizer 415 differs from a Fresnel lens. A Fresnel lens commonly focuses most or all incoming light to a central point. The top surface of each facet of a Fresnel lens retains a curvature associated with a corresponding spherical or curved lens. In contrast, the surface of each facet 632 of focusing homogenizer 415 does not retain a curvature associated with a corresponding curved lens, but rather uses prismatic effects to refract light. Thus, for example, the surfaces of a facet 632 of focusing homogenizer 415 may be flat or approximately flat.

Figure 6B:
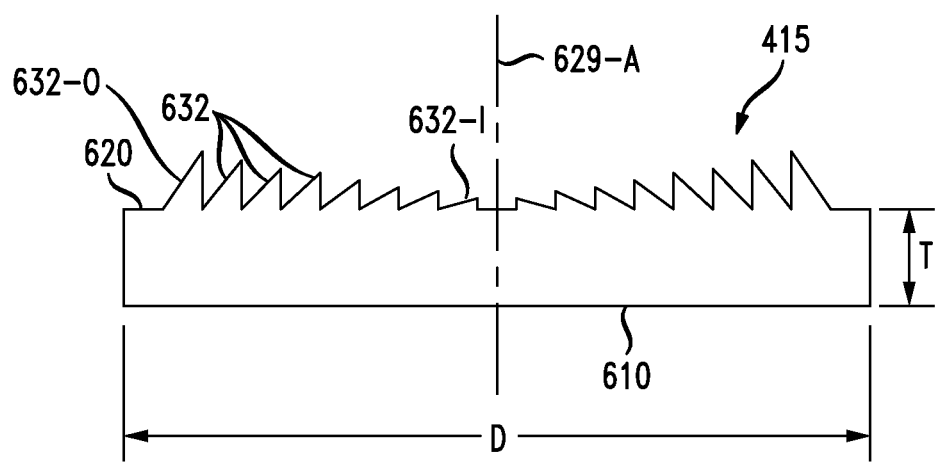
FIG. 6B shows a cross section of the focusing homogenizer of FIG. 6A.

FIG. 6B shows a cross section of focusing homogenizer 415 of FIG. 6A. Focusing homogenizer 415 comprises a first surface 610, and a second surface 620 that includes facets 632, including an inner facet 632-I and an outer facet 632-O. Facets 632 are arranged concentrically around a central axis 629-A. Focusing homogenizer 415 has a diameter D and a thickness T. The thickness T of focusing homogenizer 415 may vary. For example, in some embodiments, diameter D of focusing homogenizer 415 may be six inches or less. In one embodiment, diameter D of focusing homogenizer 415 is approximately 25 millimeters. Focusing homogenizer 415 may have other diameters as required by the optical viewing system of the device being used.

Figure 6C:
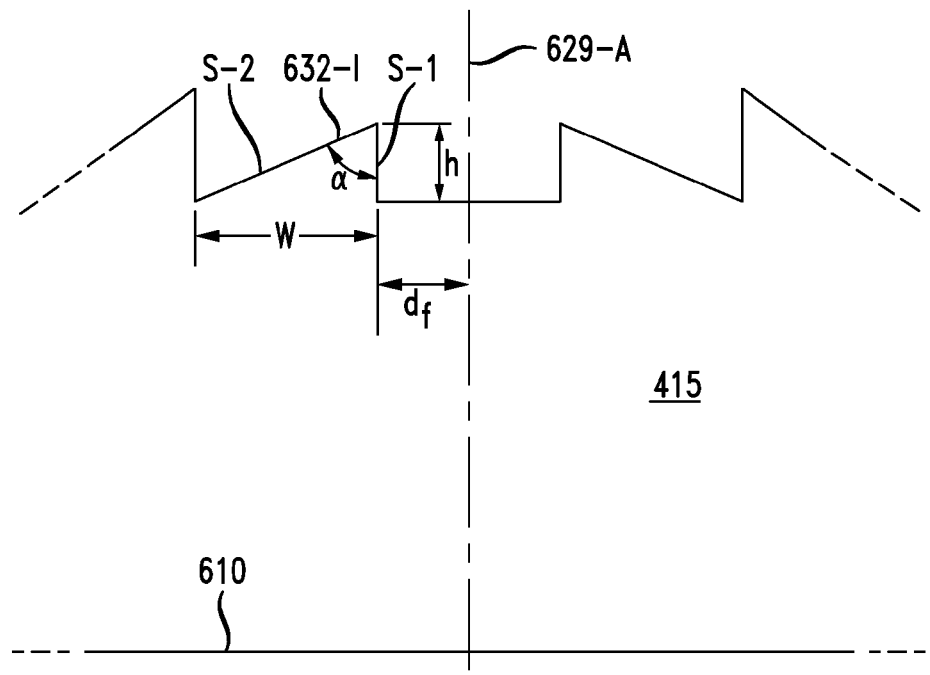
FIG. 6C shows several facets of the focusing homogenizer of FIGS. 6A-6B.

FIG. 6C shows several facets, including facet 632-I, in accordance with the embodiment of FIGS. 6A-6B. Each facet 632 is defined by various characteristics including height, width, facet angle, etc. For example, facet 632-I has a facet height h, a facet width W, and a facet angle α. A facet may have other characteristics not shown in FIG. 6C, such as radius, smoothness, reflectivity, etc.

Each facet is further defined by its distance from central axis 629-A. Referring to FIG. 6C, facet 632-I is located at a distance df from center line C (629). More specifically, distance df represents the distance between central axis 629-A and the innermost point of facet 632-I.

Referring to FIG. 6C, facet 632-I has a first, inner side S-1 and a second, outer side S-2. In this discussion, the inner side of a facet is the side closest to central axis 629-A and the outer side is the side of the facet that is farthest from central axis 629-A. In the illustrative embodiment, inner side S-1 of facet 632-I is vertical, and outer side S-2 has a sloping configuration.

While in FIG. 6C, inner side S-1 of facet 632-I is vertical and outer side S-2 of facet 632-I is sloping, other facets may be constructed differently. In some examples, where a facet having a sloping inner side is adjacent to a facet having a sloping outer side, the facets may be joined and not have a vertical side. In other embodiments, a facet may have two sloping sides and no vertical side.

In the illustrative embodiment, the surface of side S-1 and the surface of side S-2 are flat or approximately flat. The surfaces of other facets are also flat or approximately flat.

In this discussion, the facet angle α of a particular facet is the angle between side S-1 of the facet and side S-2 of the facet. For a particular facet, the value of facet angle α is negative if the inner side S-1 is the sloping side of the facet; facet angle α is positive if the outer side S-2 is the sloping side of the facet.

In the embodiment of FIGS. 6A-6C, the height of facets 632 varies. For example, the height of a facet 632 may vary based on the distance of the facet from central axis 629-A. In one embodiment, the height of inner facet 632-I is lower than the height of outer facet 632-O. The height of facets 632 may increase uniformly from inner facet 632-I to outer facet 632-O. In other embodiments, the height of facets 632 may vary non-uniformly, for example, according to a selected linear or non-linear function, or based on other factors.

The width of facets 632 may vary. In one embodiment, the width of each facet 632 is less than the overlap diameter (defined as the diameter of a region on focusing filament 425 on which the color components overlap).

The number of facets 632 may vary as well. While FIGS. 6A-6C illustrate an embodiment having a particular number of facets, in other embodiments, focusing homogenizer 415 may have a different number of facets than that shown.

Certain dimensions and characteristics of focusing homogenizer 415, such as the facet height, facet width, facet angle, thickness T, diameter D, number of facets, arrangement and shape of facets, etc., may be determined empirically based on characteristics of the slit lamp system used, the multiple color light source used, the size of the light collection area, and other factors. For example, focusing homogenizer 415 may be designed and manufactured to function with a given multiple color light source and slit lamp system. Accordingly, the number, size, and separation of facets 632 may be selected based on characteristics of multiple color light source 230, such as the number of colors/wavelengths generated, the spatial separation between the wavelengths, etc., and on characteristics of slit lamp 205, such as the size and location of one or more lenses in the slit lamp, etc. In other examples, characteristics of facets 632, such as facet angles, etc., may be selected based on working distance, the size of a desired spot or ring, available manufacturing tolerances, the number and spacing of the grooves on focusing homogenizer 415, etc.

Figure 6D:
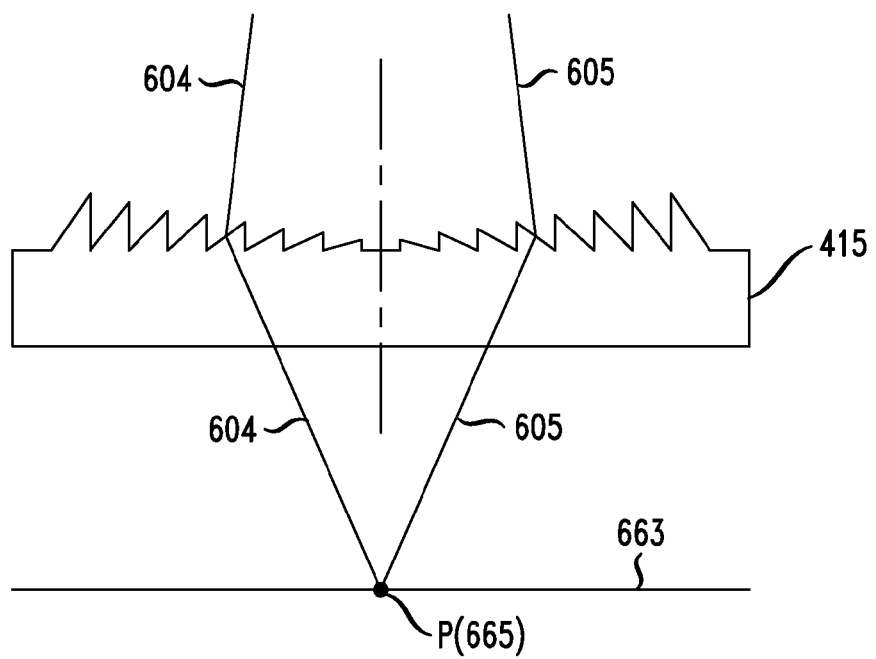
FIG. 6D shows light refracted onto a focal plane by the focusing homogenizer of FIGS. 6A-6B.

FIG. 6D shows focusing homogenizer 415 refracting and focusing beams of light 604, 605 onto a focal plane 663 in accordance with an embodiment. In this example, beams 604 and 605 are focused at a focal point P (665).

Table 1 includes data defining focusing homogenizer 415 in accordance with an embodiment. Each row of Table 1 represents, and includes data that defines, one facet of focusing homogenizer 415. Specifically, Table 1 comprises four columns specifying (1) a facet angle α, expressed in degrees, (2) a facet distance df defining a distance between the central axis 629-A of focusing homogenizer 415 and the innermost point of the facet, (3) the facet width W, and (4) the facet angle α, expressed in arcseconds.

In the embodiment defined in Table 1, all facets have positive facet angles and therefore have sloping outer sides. In other embodiments, facet angles may be selected and arranged in any combination. For example, in some embodiments, all facets may have negative facet angles. In other embodiments, the facets of the focusing homogenizer may have any combination of positive and negative facet angles.

TABLE 1

| Facet Angle α (degrees) | Facet Distance $d_f$ (mm) | Facet width W (mm) | Facet Angle α (arcseconds) |
|---|---|---|---|
| 0.466 | 0 | 0.2 | 1677.90 |
| 1.398 | 0.2 | 0.2 | 5031.82 |
| 2.328 | 0.4 | 0.2 | 8380.16 |
| 3.255 | 0.6 | 0.2 | 11719.23 |
| 4.179 | 0.8 | 0.2 | 15045.39 |
| 5.099 | 1 | 0.2 | 18355.08 |
| 6.012 | 1.2 | 0.2 | 21644.80 |
| 6.920 | 1.4 | 0.2 | 24911.19 |
| 7.820 | 1.6 | 0.2 | 28150.98 |
| 8.711 | 1.8 | 0.2 | 31361.06 |
| 9.594 | 2 | 0.2 | 34738.46 |
| 10.467 | 2.2 | 0.2 | 37680.35 |
| 11.329 | 2.4 | 0.2 | 40784.10 |
| 12.180 | 2.6 | 0.2 | 43847.23 |
| 13.019 | 2.8 | 0.2 | 46867.45 |
| 13.846 | 3 | 0.2 | 49842.66 |
| 14.659 | 3.2 | 0.2 | 52770.94 |
| 15.459 | 3.4 | 0.2 | 55650.56 |
| 16.244 | 3.6 | 0.2 | 58479.97 |
| 17.016 | 3.8 | 0.2 | 61257.82 |
| 17.773 | 4 | 0.2 | 63982.93 |
| 18.515 | 4.2 | 0.2 | 66654.31 |
| 19.242 | 4.4 | 0.2 | 69271.11 |
| 19.954 | 4.6 | 0.2 | 71832.67 |

TABLE 1-continued

| Facet Angle α (degrees) | Facet Distance d_f (mm) | Facet width W (mm) | Facet Angle α (arcseconds) |
|---|---|---|---|
| 20.650 | 4.8 | 0.2 | 74338.50 |
| 21.330 | 5 | 0.2 | 76788.22 |
| 21.995 | 5.2 | 0.2 | 79181.62 |
| 22.644 | 5.4 | 0.2 | 81518.62 |
| 23.278 | 5.6 | 0.2 | 83799.26 |
| 23.896 | 5.8 | 0.2 | 86023.69 |
| 24.498 | 6 | 0.2 | 88192.17 |
| 25.085 | 6.2 | 0.2 | 90305.08 |
| 25.656 | 6.4 | 0.2 | 92362.86 |
| 26.213 | 6.6 | 0.2 | 94366.05 |
| 26.754 | 6.8 | 0.2 | 96315.26 |
| 27.281 | 7 | 0.2 | 98211.15 |
| 27.793 | 7.2 | 0.2 | 100054.47 |
| 28.291 | 7.4 | 0.2 | 101846.01 |
| 28.774 | 7.6 | 0.2 | 103586.58 |
| 29.244 | 7.8 | 0.2 | 105277.07 |
| 29.700 | 8 | 0.2 | 106918.39 |
| 30.142 | 8.2 | 0.2 | 108511.46 |
| 30.571 | 8.4 | 0.2 | 110057.23 |
| 30.988 | 8.6 | 0.2 | 111556.70 |
| 31.392 | 8.8 | 0.2 | 113010.84 |
| 31.784 | 9 | 0.2 | 114420.66 |
| 32.163 | 9.2 | 0.2 | 115787.17 |
| 32.531 | 9.4 | 0.2 | 117111.37 |
| 32.887 | 9.6 | 0.2 | 118394.27 |
| 33.232 | 9.8 | 0.2 | 119636.89 |

Focusing Filament

Figure 7A:
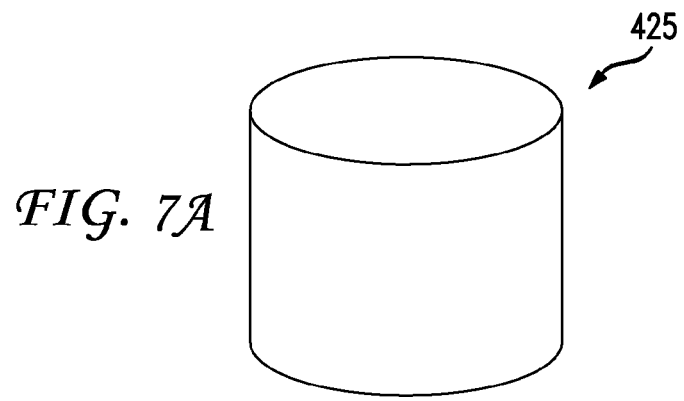
FIG. 7A shows a focusing filament in accordance with an embodiment.

FIG. 7A shows focusing filament 425 in accordance with an embodiment. Focusing filament 425 comprises a transmissive material, such as glass, plastic, etc. Other materials may be used.

Figure 7B:
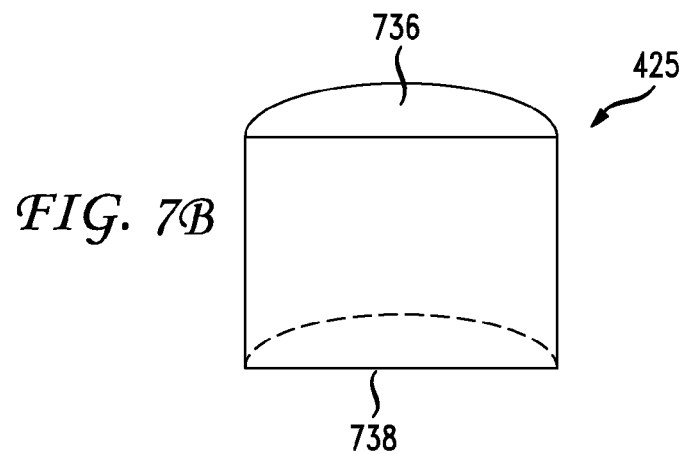
FIG. 7B shows a cross-section of the focusing filament of FIG. 7A.

FIG. 7B shows a cross-section of focusing filament 425 of FIG. 7A. Focusing filament 425 comprises a first surface 736 and a second surface 738.

Focusing filament 425 may be a lens having a size and shape selected to collect and blend the light produced by focusing homogenizer 415 and emit the light to slit lamp 205. The size and shape of focusing filament 425 may be determined empirically based on the type and configuration of slit lamp 205, for example.

In one embodiment, focusing filament 425 is a zero-power lens. For example, in one embodiment, focusing filament 425 is a cylindrical piece of clear glass. In other embodiments, focusing filament 425 may be another type of lens.

Figure 7C:
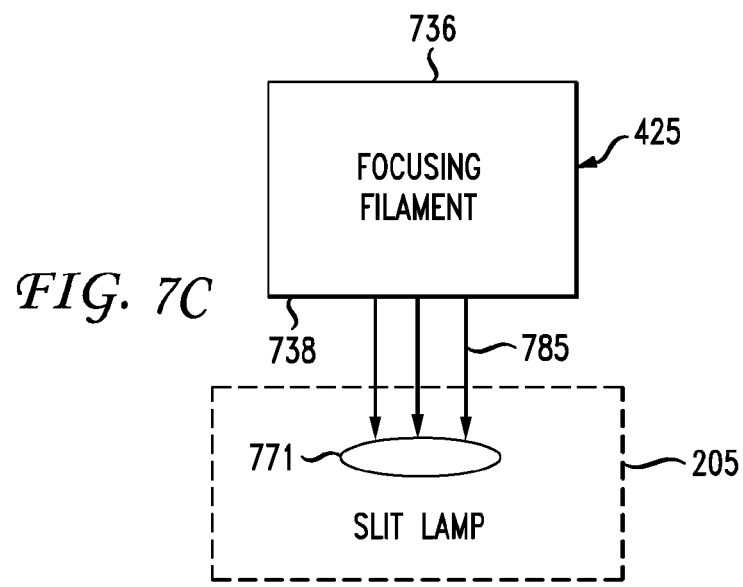
FIG. 7C shows a focusing filament and an optical element of a slit lamp in accordance with an embodiment.

FIG. 7C shows a focusing filament and an optical element of a slit lamp in accordance with an embodiment. Referring to FIG. 7C, focusing filament 425 is configured to maintain the focusing aspect of slit lamp 205, such as by emitting uniform light 785 via second surface 738 to optical element 771 of slit lamp 205.

In other embodiments, focusing homogenizer 415 and focusing filament 425 may be used to provide uniform light for other types of imaging systems. For example, the systems, apparatus, and methods described herein may be used to provide uniform light to any imaging system in which focused light is used.

Figure 8:
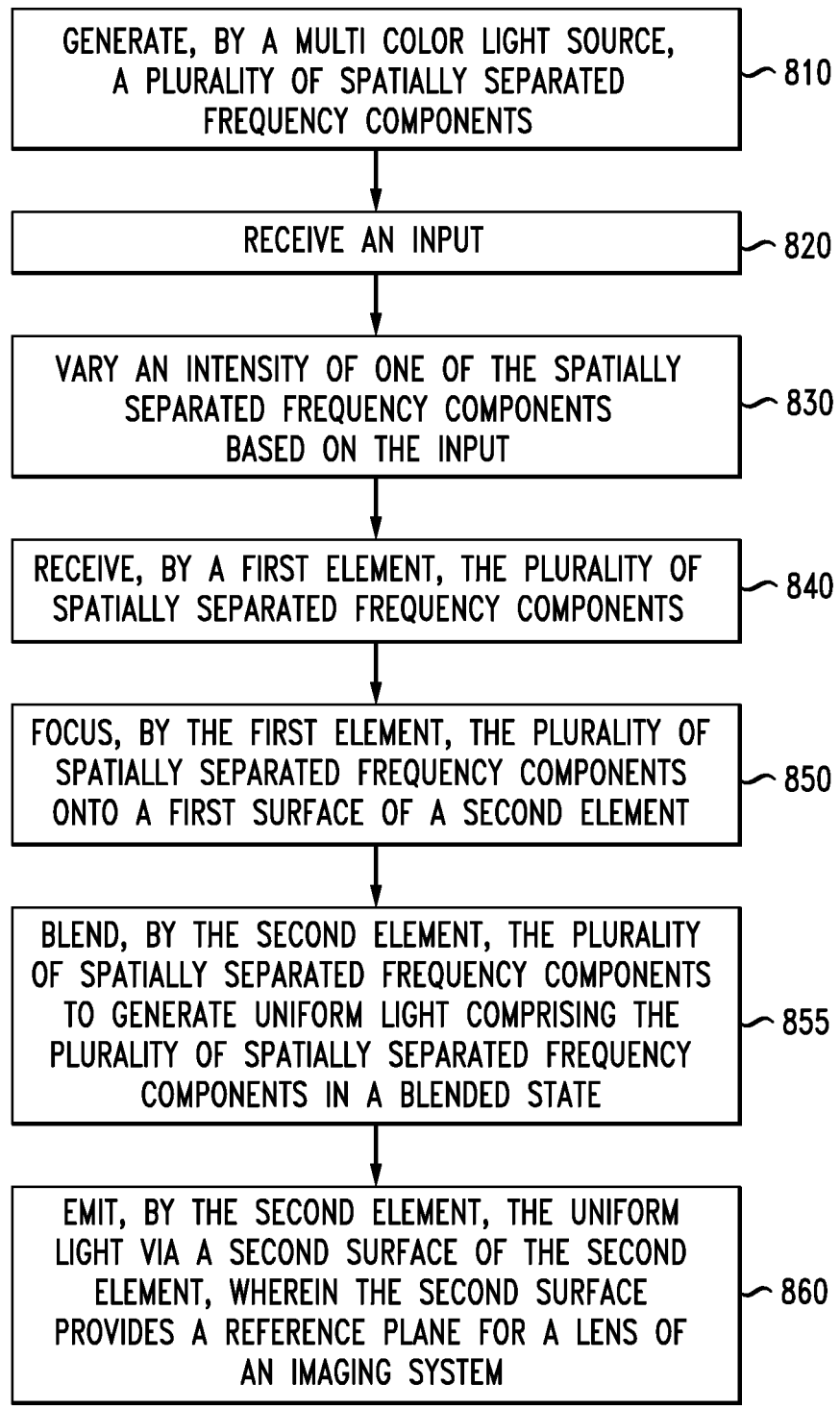
FIG. 8 is a flowchart of a method in accordance with an embodiment.

FIG. 8 is a flowchart of a method in accordance with an embodiment. The method outlined in FIG. 8 is discussed below with reference to the embodiment of FIG. 3B and with reference to FIG. 5.

At step 810, a plurality of spatially separated color components are generated by a multiple color light source. Referring to FIG. 3B and as illustrated by FIG. 5, light source 332 (of multiple color light source 230-B) generates a first color component 510-R having wavelengths associated with red, light source 334 generates a second color component 510-G having wavelengths associated with green, light source 336 generates a third color component 510-B having wavelengths associated with blue, and light source 338 generates a fourth color component 510-A having wavelengths associated with amber. As shown in FIG. 5, color components 510-R, 510-G, 510-B, and 510-A are in a spatially separated state when generated by light sources 332, 334, 336, 338.

At step 820, an input is received. For example, a practitioner wishing to use red light to illuminate a patient's retina may turn a dial to increase the intensity of red light generated by light source 332. The practitioner's input may be in the form of a command, a selection of an option, a selection of an indicator or icon, a signal, etc. The practitioner may also decrease the intensity of other wavelengths. Interface 381-B receives the practitioner's input, and generates and transmits to controller 381-B control signals corresponding to such input. Controller 380-B receives the control signals from interface 381-B.

At step 830, an intensity of one, or more than one, or none, of the color components is varied based on the input. Controller 380-B receives the control signals(s) and, in response, controls light source 332 to increase the intensity of red light. Controller 380-B may also control the other light sources appropriately, in response to the control signal(s).

At step 840, the plurality of spatially separated color components are received by a first element. Referring again to FIG. 5, color components 510-R, 510-G, 510-B, and 510-A, generated by multiple color light source 230-B in a spatially separated state, are received by focusing homogenizer 415.

At step 850, the plurality of spatially separated color components are focused, by the first element, onto a first surface of a second element. Focusing homogenizer 415 focuses color components 510-R, 510-G, 510-B, and 510-A onto first surface 736 of focusing filament 425. In one embodiment, focusing homogenizer 415 focuses the various color components 510 onto first surface 736 of focusing filament 425 such that the color components overlap within a selected region of first surface 736. The diameter of the selected region may be referred to as the overlap diameter.

At step 855, the plurality of spatially separated color components are blended, by the second element, to generate uniform light comprising the plurality of spatially separated color components in a blended state. Because color components 510-R, 510-G, 510-B, and 510-A overlap on a selected region of first surface 736, the plurality of color components are in a blended state at surface 736 of focusing filament, and are transmitted within focusing filament 425 from first surface 736 to second surface 738 in a blended state.

At step 860, uniform light is emitted, by the second element, via a second surface of the second element, wherein the second surface provides a reference plane for a lens of an imaging system. Color components 510-R, 510-G, 510-B, and 510-A are transmitted within focusing filament 425 to second surface 738 in a blended state, and emitted via surface 738 as uniform light 520. In one embodiment, second surface 738 serves as a reference plane for a lens (or a mirror) within slit lamp 205. FIG. 7C shows focusing filament 725 and an optical component 771 of slit lamp 205 in accordance with an embodiment. In this example, multiple color components are received by focusing filament 425 via first surface 736, as discussed above. The plurality of color components are transmitted within focusing filament 425 from first surface 736 to second surface 738, in a blended state, and emitted via second surface 738 as uniform light 785. Optical component 771, which may be a lens or mirror within slit lamp 205, for example, uses second surface 738 of focusing filament 425 as a reference plane, and receives uniform light 785.

In various embodiments, the method steps described herein, including the method steps described in FIG. 8, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 8, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 9:
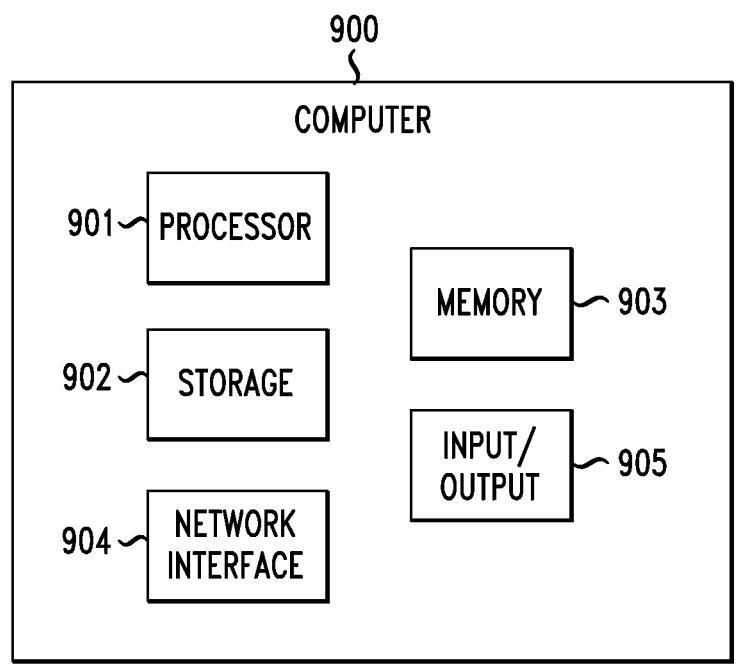
FIG. 9 shows components of an exemplary computer that may be used to implement certain embodiments of the invention.

A high-level block diagram of an exemplary computer that may be used to implement systems, apparatus and methods described herein is illustrated in FIG. 9. Computer 900 comprises a processor 901 operatively coupled to a data storage device 902 and a memory 903. Processor 901 controls the overall operation of computer 900 by executing computer program instructions that define such operations. The computer program instructions may be stored in data storage device 902, or other computer readable medium, and loaded into memory 903 when execution of the computer program instructions is desired. Thus, the method steps of FIG. 8 can be defined by the computer program instructions stored in memory 903 and/or data storage device 902 and controlled by the processor 901 executing the computer program instructions. For example, the computer program instructions can be implemented as computer executable code programmed by one skilled in the art to perform an algorithm defined by the method steps of FIG. 8. Accordingly, by executing the computer program instructions, the processor 901 executes an algorithm defined by the method steps of FIG. 8. Computer 900 also includes one or more network interfaces 904 for communicating with other devices via a network. Computer 900 also includes one or more input/output devices 905 that enable user interaction with computer 900 (e.g., display, keyboard, mouse, speakers, buttons, etc.).

Processor 901 may include both general and special purpose microprocessors, and may be the sole processor or one of multiple processors of computer 900. Processor 901 may comprise one or more central processing units (CPUs), for example. Processor 901, data storage device 902, and/or memory 903 may include, be supplemented by, or incorporated in, one or more application-specific integrated circuits (ASICs) and/or one or more field programmable gate arrays (FPGAs).

Data storage device 902 and memory 903 each comprise a tangible non-transitory computer readable storage medium. Data storage device 902, and memory 903, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 905 may include peripherals, such as a printer, scanner, display screen, etc. For example, input/output devices 905 may include a display device such as a cathode ray tube (CRT) or liquid crystal display (LCD) monitor for displaying information to the user, a keyboard, and a pointing device such as a mouse or a trackball by which the user can provide input to computer 900.

Any or all of the systems and apparatus discussed herein, including multiple color light source 230, controller 380, interface 381, etc., may be implemented using a computer such as computer 900.

One skilled in the art will recognize that an implementation of an actual computer or computer system may have other structures and may contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A system comprising:
a first element, comprising a central point and a plurality of facets arranged concentrically around the central point, each facet having a respective height that varies based on a distance from the central point, wherein the first element is configured to:
  receive a plurality of spatially separated color components, wherein each of the plurality of color components comprises light of a respective wavelength; and
  focus the plurality of spatially separated color components onto a first surface of a second element;
a second element comprising a first surface and a second surface, wherein the second element is configured to:
  receive the plurality of color components via the first surface;
  transmit to the second surface uniform light comprising the plurality of color components in a blended state; and
  emit the uniform light via the second surface.

2. The system of claim 1, further comprising:
a multiple-color light source configured to generate a plurality of spatially separated color components.

3. The system of claim 2, wherein the multiple-color light source further comprises:
a plurality of light sources, wherein each light source is configured to generate a color component associated with a respective wavelength; and
a controller configured to control an intensity of the color component generated by at least one light source.

4. The system of claim 3, wherein the plurality of light sources comprises a plurality of LED light sources.

5. The system of claim 3, wherein the plurality of light sources comprise:
a first light source configured to generate a first color component associated with a red wavelength;
a second light source configured to generate a second color component associated with a green wavelength;
a third light source configured to generate a third color component associated with a blue wavelength; and
a fourth light source configured to generate a fourth color component associated with an amber wavelength.

6. The system of claim 1, wherein the second surface provides a reference plane for an optical element of an imaging system.

7. The system of claim 6, wherein the optical element comprises one of a lens and a mirror.

8. The system of claim 6, wherein the imaging system comprises a slit lamp.

9. The system of claim 8, wherein the second element is further configured to:
maintain the focusing aspect of the slit lamp.

10. The system of claim 1, wherein each facet of the plurality of facets is comprised of a plurality of surfaces and each surface of the plurality of surfaces is flat.

11. The system of claim 10, wherein at least one facet has an inner side that is vertical and a second side that has a sloping configuration.

12. A method comprising:
receiving, by a first element, a plurality of spatially separated color components, the first element comprising a central point and a plurality of facets arranged concentrically around the central point, each facet having a respective height that varies based on a distance from the central point;
focusing, by the first element, the plurality of spatially separated color components onto a first surface of a second element;
blending, by the second element, the plurality of spatially separated color components, to generate uniform light comprising the plurality of color components in a blended state;
emitting, by the second element, via a second surface of the second element, the uniform light,
wherein the second surface provides a reference plane for an optical element of an imaging system.

13. The method of claim 12, further comprising:
generating, by a multiple color light source, a plurality of spatially separated color components.

14. The method of claim 13, further comprising:
generating a first color component having a wavelength associated with red;
generating a second color component having a wavelength associated with green; and
generating a third color component having a wavelength associated with blue.

15. The method of claim 14, further comprising:
receiving an input; and
varying an intensity of one of the first, second, and third color components based on the input.

16. The method of claim 12, wherein each facet of the plurality of facets is comprised of a plurality of surfaces and each surface of the plurality of surfaces is flat.

17. A system comprising:
a light source configured to generate a plurality of spatially separated color components;
a first element comprising a transmissive material, a central point and a plurality of facets, the plurality of facets arranged concentrically around the central point, each facet having a respective height that varies based on a distance from the central point, the first element configured to refract the plurality of spatially separated color components onto a surface of a second element;
the second element comprising a transmissive material, the second element configured to blend the plurality of color components to produce uniform light, and provide the uniform light to a slit lamp; and
a slit lamp;
wherein the light source is further configured to:
receive an input indicating a change in an intensity of a selected one of the plurality of spatially separated color components; and
modify the intensity of the selected one of the plurality of spatially separated color components, based on the input.

18. The system of claim 17, wherein the light source is a multiple color light source comprising a plurality of LED light sources.

19. The system of claim 18, wherein each facet of the plurality of facets is comprised of a plurality of surfaces and each surface of the plurality of surfaces is flat.

20. The system of claim 17, wherein the first element comprises a focusing homogenizer and the second element comprises a focusing filament.

* * * * *